United States Patent
Pool et al.

(10) Patent No.: US 9,186,183 B2
(45) Date of Patent: Nov. 17, 2015

(54) MAINTENANCE FEATURE IN MAGNETIC IMPLANT

(71) Applicant: ELLIPSE TECHNOLOGIES, INC., Irvine, CA (US)

(72) Inventors: Scott Pool, Laguna Hills, CA (US); Arvin Chang, Yorba Linda, CA (US)

(73) Assignee: Ellipse Technologies, Inc., Aliso Viejo, CA (US)

( * ) Notice: Subject to any disclaimer, the term of this patent is extended or adjusted under 35 U.S.C. 154(b) by 0 days.

(21) Appl. No.: 14/250,313

(22) Filed: Apr. 10, 2014

(65) Prior Publication Data

US 2014/0222075 A1  Aug. 7, 2014

Related U.S. Application Data

(63) Continuation of application No. 13/198,571, filed on Aug. 4, 2011, now Pat. No. 8,734,488.

(60) Provisional application No. 61/372,020, filed on Aug. 9, 2010.

(51) Int. Cl.
*A61B 17/70* (2006.01)

(52) U.S. Cl.
CPC .................................. *A61B 17/7016* (2013.01)

(58) Field of Classification Search
CPC ........... A61B 17/7014; A61B 17/7017; A61B 17/7016; A61B 17/7019; A61B 17/702; A61B 17/7025; A61B 17/025; A61B 2017/0256
USPC ............ 606/251–253, 258–261, 278, 105, 90
See application file for complete search history.

(56) References Cited

U.S. PATENT DOCUMENTS

| 3,377,576 | A | * | 4/1968 | Langberg et al. | 335/196 |
| 5,480,437 | A | * | 1/1996 | Draenert | 623/23.52 |
| 5,575,790 | A | * | 11/1996 | Chen et al. | 606/60 |
| 6,319,255 | B1 | * | 11/2001 | Grundei et al. | 606/76 |
| 6,375,682 | B1 | | 4/2002 | Fleischmann et al. | |
| 6,416,516 | B1 | | 7/2002 | Stauch et al. | |
| 6,706,042 | B2 | | 3/2004 | Taylor | |

(Continued)

FOREIGN PATENT DOCUMENTS

DE  102007053362 A1 * 5/2009 ............... A61F 2/30

OTHER PUBLICATIONS

PCT International Search Report for PCT/US2011/046655 dated Mar. 13, 2012 in 6 pages.

(Continued)

*Primary Examiner* — Eduardo C Robert
*Assistant Examiner* — Julianna N Harvey
(74) *Attorney, Agent, or Firm* — Knobbe, Martens, Olson & Bear, LLP

(57) ABSTRACT

A distraction system includes a distraction rod having one end configured for affixation to at a first location on patient. The system further includes an adjustable portion configured for placement in the patient at a second location, the adjustable portion comprising a housing containing a magnetic assembly comprising a magnet, the magnetic assembly secured to a threaded element that interfaces with an opposing end of the distraction rod. The system includes a magnetically permeable member in proximity to the magnetic assembly and covering an arc of less than 360° of the adjustable portion.

15 Claims, 12 Drawing Sheets

(56) References Cited

U.S. PATENT DOCUMENTS

| | | |
|---|---|---|
| 7,063,706 B2 | 6/2006 | Wittenstein |
| 7,357,635 B2 | 4/2008 | Belfor et al. |
| 7,458,981 B2 | 12/2008 | Fielding et al. |
| 7,531,002 B2 | 5/2009 | Sutton et al. |
| 7,601,156 B2 | 10/2009 | Robinson |
| 7,611,526 B2 | 11/2009 | Carl et al. |
| 7,666,184 B2 | 2/2010 | Stauch |
| 7,753,915 B1 * | 7/2010 | Eksler et al. .................. 606/105 |
| 7,776,091 B2 | 8/2010 | Mastrorio et al. |
| 7,794,476 B2 | 9/2010 | Wisnewski |
| 7,811,328 B2 | 10/2010 | Molz, IV et al. |
| 7,887,566 B2 | 2/2011 | Hynes |
| 8,043,299 B2 | 10/2011 | Conway |
| 8,105,363 B2 | 1/2012 | Fielding et al. |
| 8,147,517 B2 | 4/2012 | Trieu et al. |
| 8,147,549 B2 | 4/2012 | Metcalf et al. |
| 8,177,789 B2 | 5/2012 | Magill et al. |
| 8,211,179 B2 | 7/2012 | Molz, Iv et al. |
| 8,216,275 B2 | 7/2012 | Fielding et al. |
| 8,221,420 B2 | 7/2012 | Keller |
| 8,241,331 B2 | 8/2012 | Arnin |
| 8,252,063 B2 | 8/2012 | Stauch |
| 8,298,240 B2 | 10/2012 | Giger et al. |
| 8,419,801 B2 | 4/2013 | DiSilvestro et al. |
| 8,439,915 B2 | 5/2013 | Harrison et al. |
| 8,469,908 B2 | 6/2013 | Asfora |
| 8,486,110 B2 | 7/2013 | Fielding et al. |
| 8,529,606 B2 | 9/2013 | Alamin et al. |
| 8,562,653 B2 | 10/2013 | Alamin et al. |
| 8,568,457 B2 | 10/2013 | Hunziker |
| 8,632,544 B2 | 1/2014 | Haaja |
| 8,641,723 B2 | 2/2014 | Connor |
| 8,663,285 B2 | 3/2014 | Dall et al. |
| 8,734,488 B2 | 5/2014 | Pool et al. |
| 8,777,947 B2 | 7/2014 | Zahrly et al. |
| 8,870,959 B2 | 10/2014 | Arnin |
| 8,894,663 B2 | 11/2014 | Giger et al. |
| 8,968,406 B2 | 3/2015 | Arnin |
| 8,992,527 B2 | 3/2015 | Guichet |
| 2004/0023623 A1 | 2/2004 | Stauch |
| 2004/0030395 A1 * | 2/2004 | Blunn et al. ............... 623/18.12 |
| 2005/0090823 A1 | 4/2005 | Bartim |
| 2005/0159754 A1 | 7/2005 | Odrich |
| 2006/0047282 A1 * | 3/2006 | Gordon .......................... 606/61 |
| 2006/0235299 A1 | 10/2006 | Martinelli |
| 2006/0235424 A1 | 10/2006 | Vitale et al. |
| 2006/0293683 A1 | 12/2006 | Stauch |
| 2007/0010814 A1 | 1/2007 | Stauch |
| 2007/0264605 A1 | 11/2007 | Belfor et al. |
| 2008/0033436 A1 | 2/2008 | Song et al. |
| 2008/0161933 A1 | 7/2008 | Grotz et al. |
| 2008/0167685 A1 | 7/2008 | Allard et al. |
| 2008/0228186 A1 | 9/2008 | Gall et al. |
| 2008/0255615 A1 | 10/2008 | Vittur et al. |
| 2009/0012565 A1 | 1/2009 | Sachs et al. |
| 2009/0076597 A1 | 3/2009 | Dahlgren et al. |
| 2009/0093890 A1 | 4/2009 | Gelbart |
| 2009/0112207 A1 | 4/2009 | Walker et al. |
| 2009/0112263 A1 | 4/2009 | Pool et al. |
| 2009/0171356 A1 | 7/2009 | Klett |
| 2009/0192514 A1 | 7/2009 | Feinberg et al. |
| 2009/0248148 A1 | 10/2009 | Shaolian et al. |
| 2010/0094302 A1 | 4/2010 | Pool et al. |
| 2010/0100185 A1 | 4/2010 | Trieu et al. |
| 2010/0114103 A1 | 5/2010 | Harrison et al. |
| 2010/0121323 A1 | 5/2010 | Pool et al. |
| 2010/0249847 A1 | 9/2010 | Jung et al. |
| 2011/0257655 A1 | 10/2011 | Copf |
| 2012/0004494 A1 | 1/2012 | Payne et al. |
| 2012/0203282 A1 | 8/2012 | Sachs et al. |
| 2012/0283781 A1 | 11/2012 | Arnin |
| 2014/0005788 A1 | 1/2014 | Haaja et al. |
| 2014/0142631 A1 | 5/2014 | Hunziker |
| 2014/0324047 A1 | 10/2014 | Zahrly et al. |
| 2015/0105824 A1 | 4/2015 | Moskowitz et al. |

OTHER PUBLICATIONS

PCT Written Opinion of the International Search Authority for PCT/US2011/046655 dated Mar. 13, 2012 (4 pages).

EPO Translation of DE 102007053362; accessed on May 31, 2013.

* cited by examiner

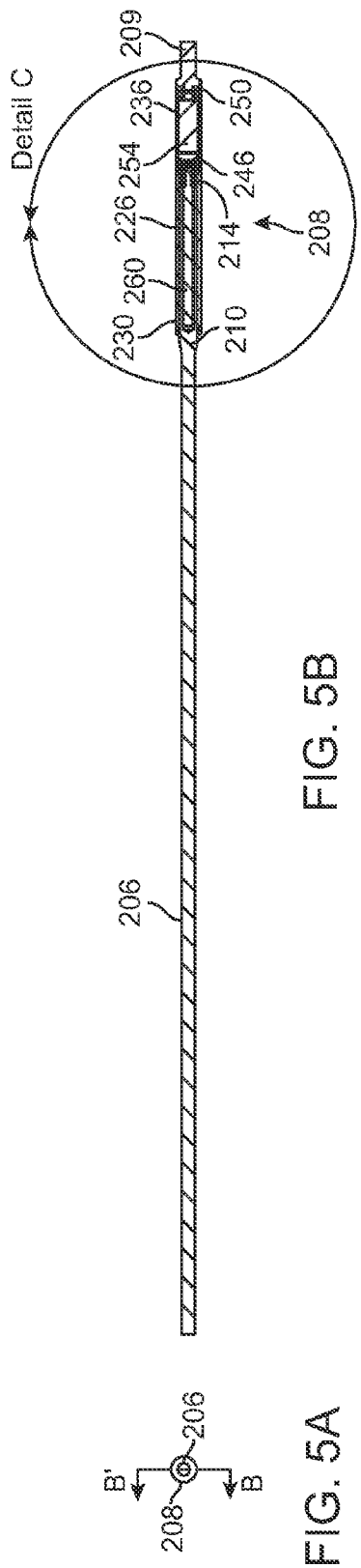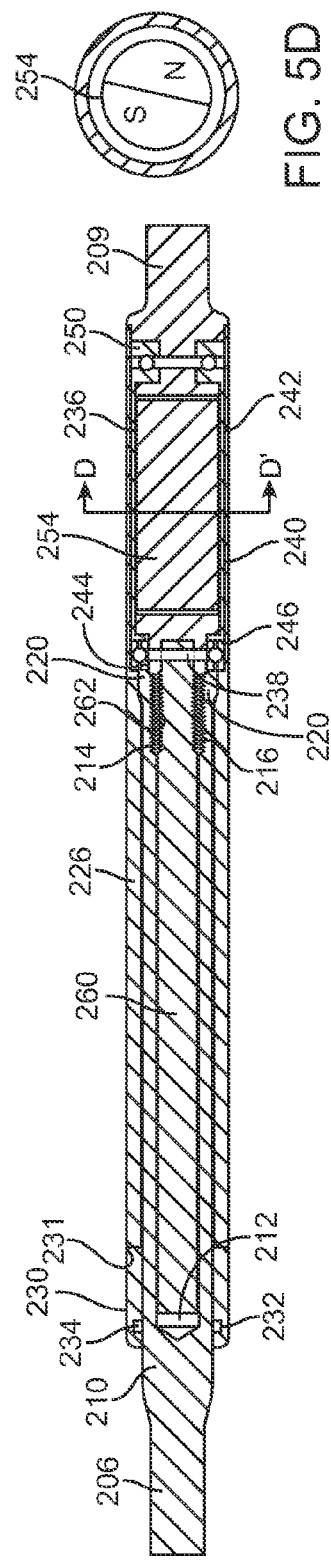

MAINTENANCE FEATURE IN MAGNETIC IMPLANT

RELATED APPLICATION

Any and all applications for which a foreign or domestic priority claim is identified in the Application Data Sheet as filed with the present application are hereby incorporated by reference under 37 CFR 1.57.

FIELD OF THE INVENTION

The field of the invention generally relates to medical devices for treating disorders of the skeletal system.

BACKGROUND

Scoliosis is a general term for the sideways (lateral) curving of the spine, usually in the thoracic or thoracolumbar region. Often, there is also a rotation of the spine as well as curvature. Scoliosis is commonly broken up into different treatment groups. Adolescent Idiopathic Scoliosis, Early Onset Scoliosis and Adult Scoliosis.

Adolescent idiopathic Scoliosis (AIS) typically affects children between ages 10 and 16, and becomes most severe during growth spurts that occur as the body is developing. One to two percent of children between ages 10 and 16 have some amount of scoliosis. Of every 1000 children, two to five develop curves that are serious enough to require treatment. The degree of scoliosis is typically described by the Cobb angle, which is determined, usually from x-ray images, by taking the most tilted vertebrae above and below the apex of the curved portion and measuring the angle between intersecting lines draw perpendicular to the top of the top vertebrae and the bottom of the bottom. The term idiopathic refers to the fact that the exact cause of this curvature is unknown. Some have speculated that scoliosis occurs when, during rapid growth phases, the ligamentum flavum of the spine is too tight and hinders symmetric growth of the spine. For example, as the anterior portion of the spine elongates faster than the posterior portion, the thoracic spine begins to straighten, until it curves laterally, often with an accompanying rotation. In more severe cases, this rotation actually creates a noticeable deformity, wherein one shoulder is lower than the other. Currently, many school districts perform external visual assessment of spines, for example in all fifth grade students. For those students in whom an "S" shape or "C" shape is identified, instead of an "I" shape, a recommendation is given to have the spine examined by a physician, and commonly followed-up with periodic spinal x-rays.

Typically, patients with a Cobb angle of 20° or less are not treated, but are continually followed up, often with subsequent x-rays. Patients with a Cobb angle of 40° or greater are usually recommended for fusion surgery. It should be noted that many patients do not receive this spinal assessment, for numerous reasons. Many school districts do not perform this assessment, and many children do not regularly visit a physician, so often, the curve progresses rapidly and severely. There is a large population of grown adults with untreated scoliosis, in extreme cases with a Cobb angle as high as or greater than 90°. Many of these adults, though, do not have pain associated with this deformity, and live relatively normal lives, though oftentimes with restricted mobility and motion. In AIS, the ratio of females to males for curves under 10° is about one to one, however, at angles above 30°, females outnumber males by as much as eight to one. Fusion surgery can be performed on the AIS patients or on adult scoliosis patients. In a typical posterior fusion surgery, an incision is made down the length of the back and Titanium or stainless steel straightening rods are placed along the curved portion. These rods are typically secured to the vertebral bodies, for example with bone screws, or more specifically pedicle screws, in a manner that allows the spine to be straightened. Usually, at the section desired for fusion, the intervertebral disks are removed and bone graft material is placed to create the fusion. If this is autologous material, the bone is harvested from a hip via a separate incision.

Alternatively, the fusion surgery may be performed anteriorly. A lateral and anterior incision is made for access. Usually, one of the lungs is deflated in order to allow access to the spine from this anterior approach. In a less-invasive version of the anterior procedure, instead of the single long incision, approximately live incisions, each about three to four cm long are made in several of the intercostal spaces (between the ribs) on one side of the patient. In one version of this minimally invasive surgery, tethers and bone screws are placed and are secured to the vertebra on the anterior convex portion of the curve. Currently, clinical trials are being performed which use staples in place of the tether/screw combination. One advantage of this surgery in comparison with the posterior approach is that the scars from the incisions are not as dramatic, though they are still located in a visible area, when a bathing suit, for example, is worn. The staples have had some difficulty in the clinical trials. The staples tend to pull out of the bone when a critical stress level is reached.

Commonly, after surgery, the patient will wear a brace for a few months as the fusing process occurs. Once the patient reaches spinal maturity, it is difficult to remove the rods and associated hardware in a subsequent surgery, because the fusion of the vertebra usually incorporates the rods themselves. Standard practice is to leave this implant in for life. With either of these two surgical methods, after fusion, the patient's spine is now straight, but depending on how many vertebra were fused, there are often limitations in the degree of flexibility, both in bending and twisting. As these fused patients mature, the fused section can impart large stresses on the adjacent non-fused vertebra, and often, other problems including pain can occur in these areas, sometimes necessitating further surgery. Many physicians are how interested in fusionless surgery for scoliosis, which may be able to eliminate some of the drawbacks of fusion.

One group of patients in which the spine is especially dynamic is the subset known as Early Onset Scoliosis (EOS), which typically occurs in children before the age of five. This is a more rare condition, occurring in only about one or two out of 10,000 children, but can be severe, sometimes affecting the normal development of organs. Because of the fact that the spines of these children will still grow a large amount after treatment, non-fusion distraction devices known as growing rods and a device known as the VEPTR—Vertical Expandable Prosthetic Titanium. Rib ("Titanium Rib") have been developed. These devices are typically adjusted approximately every six months, to match the child's growth, until the child is at least eight years old, sometimes until they are 15 years old. Each adjustment requires a surgical incision to access the adjustable portion of the device. Because the patients may receive the device at an age as early as six months old, this treatment requires a large number of surgeries. Because of the multiple surgeries, these patients have a rather high preponderance of infection and other complications.

Returning to the AIS patients, the treatment methodology for those with a Cobb angle between 20° and 40° is quite controversial. Many physicians prescribe a brace (for example, the Boston Brace), that the patient must wear on their body and under their clothes 18 to 23 hours a day until they become skeletally mature, for example to age 16. Because these patients are all passing through their socially demanding adolescent years, it is quite a serious prospect to be forced with the choice of either wearing a somewhat bulky brace that covers most of the upper body, having fusion surgery that may leave large scars and also limit motion, or doing nothing and running the risk of becoming disfigured and possibly disabled. It is commonly known that many patients have at times hidden their braces, for example, in a bush outside of school, in order to escape any related embarrassment. The patient compliance with brace wearing has been so problematic, that there have been special braces constructed which sense the body of the patient, and keep track of the amount of time per day that the brace is worn. Patients have even been known to place objects into unworn braces of this type in order to fool the sensor. Coupled with the inconsistent patient compliance with brace usage, is a feeling by many physicians that braces, even if used properly, are not at all effective at curing scoliosis. These physicians may agree that bracing can possibly slow down or even temporarily stop curve (Cobb angle) progression, but they have noted that as soon as the treatment period ends and the brace is no longer worn, often the scoliosis rapidly progresses, to a Cobb angle even more severe than it was at the beginning of treatment. Some say the reason for the supposed ineffectiveness of the brace is that it works only on a portion of the torso, and not on the entire spins. Currently a 500 patient clinical trial known as BrAIST (Bracing in Adolescent Idiopathic Scoliosis Trial) is enrolling patients, 50% of whom will be treated with the brace and 50% of who will simply be watched. The Cobb angle data will be measured continually up until skeletal maturity, or until a Cobb angle of 50° is reached, at which time the patient will likely undergo surgery.

Though this trial began as a randomized trial, it has since been changed to a "preference" trial, wherein the patients choose which treatment arm they will be in. This is partially because so many patients were rejecting the brace. Many physicians feel that the BrAIST trial will show that braces are completely ineffective. If this is the case, the quandary about what to do with AIS patients who have a Cobb angle of between 20° and 40° will only become more pronounced. It should be noted that the "20° to 40°" patient population is as much as ten times larger than the "40° and greater" patient population.

Currently, genetic scientists have found and continue to find multiple genes that may predispose scoliosis. Though gene tests have been developed, including a scoliosis score for risk of curve progression, some are still skeptical as to whether gene therapy would be possible to prevent scoliosis. However the existence of a scoliosis gene would no doubt allow for easier and earlier identification of probable surgical patients.

SUMMARY

In one aspect of the invention, a distraction system includes a distraction rod having one end configured for affixation to at a first location on patient. The system further includes an adjustable portion configured for placement in the patient at a second location, the adjustable portion comprising a housing containing a magnetic assembly comprising a magnet, the magnetic assembly secured to a threaded element that interfaces with an opposing end of the distraction rod. The system further includes a magnetically permeable member in proximity to the magnetic assembly and covering an arc of less than 360° of the adjustable portion.

In another aspect of the invention, a method for locating a distraction system implanted within a patient using a compass having a magnetized pointer includes placing the compass in proximity to an area of the patient's skin near an expected location of the magnet of the distraction system, and observing the direction that a magnetized pointer of the compass points. The magnetized pointer is then used to confirm it is pointing to the expected location of the magnet.

BRIEF DESCRIPTION OF THE DRAWINGS

FIG. 5A is a cross-sectional view of a distraction rod and adjustable portion taken along a perpendicular axis to the longitudinal axis of the distraction rod.

FIG. 5B illustrates a cross-sectional view of the distraction rod and the adjustable portion taken along the line B'-B of FIG. 5A.

FIG. 5C illustrates an enlarged cross-sectional view of detail C of FIG. 5B.

FIG. 5D illustrates a cross-sectional view of the magnet portion of the device, taken along the line D-D' of FIG. 5C.

DETAILED DESCRIPTION OF THE ILLUSTRATED EMBODIMENTS

Figure 1:
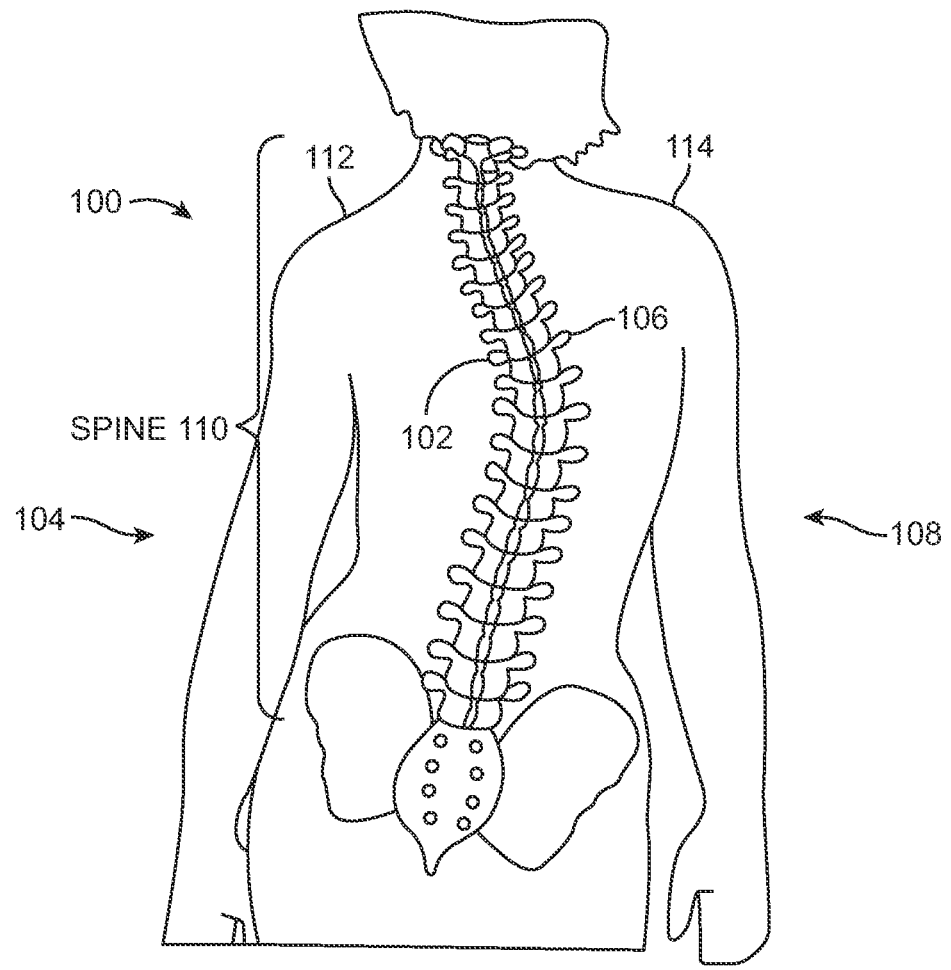
FIG. 1 illustrates the spine of a person with scoliosis.

FIG. 1 illustrates a patient 100 with scoliosis. The concave portion 102 of the spinal curve can be seen on the left side 104 of the patient 100, and the convex portion 106 can be seen on the right side 108 of the patient 100. Of course, in other patients, the concave portion 102 may appear on the right side 108 of the patient 100 while the convex portion 106 may be found on the left side 104 of the patient. In addition, as seen in FIG. 1, some rotation of the spine 110 is present, and unevenness between the left shoulder 112 and right shoulder 114 is seen.

Figure 2:
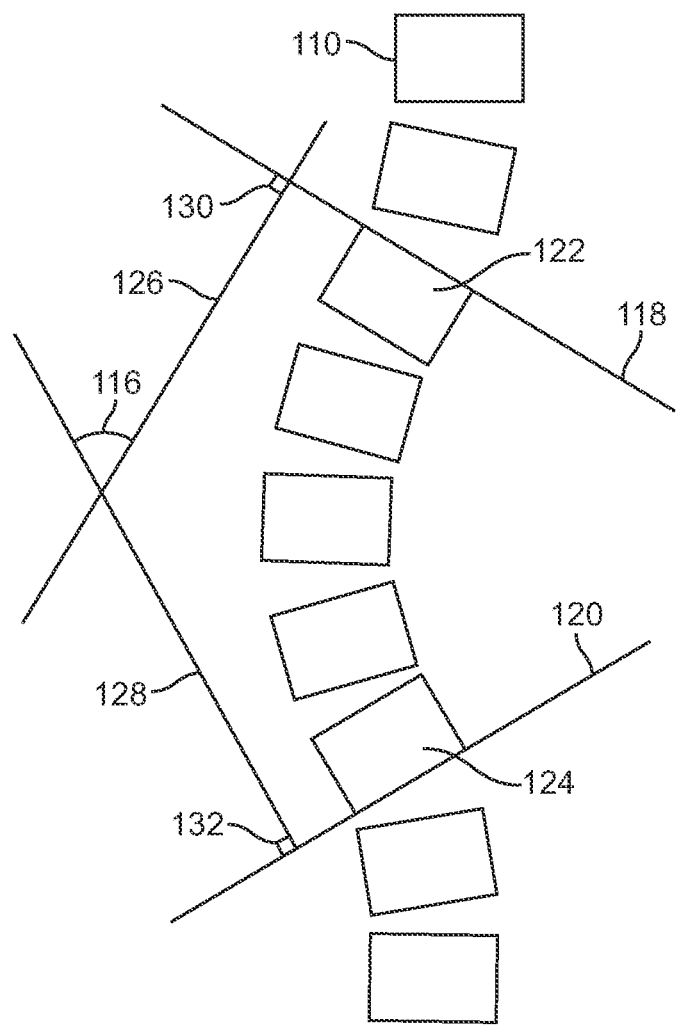
FIG. 2 illustrates the Cobb angle of a scoliotic spine.

FIG. 2 illustrates the Cobb angle 116 of a spine 110 of a patient with scoliosis. To determine the Cobb angle, lines 118 and 120 are drawn from vertebra 122 and 124, respectively. Intersecting perpendicular lines 126 and 128 are drawn by creating 90° angles 130 and 132 from lines 118 and 120. The angle 116 created from the crossing of the perpendicular lines 126 and 128 is defined as the Cobb angle. In a perfectly straight spine, this angle is 0°.

Figure 3:
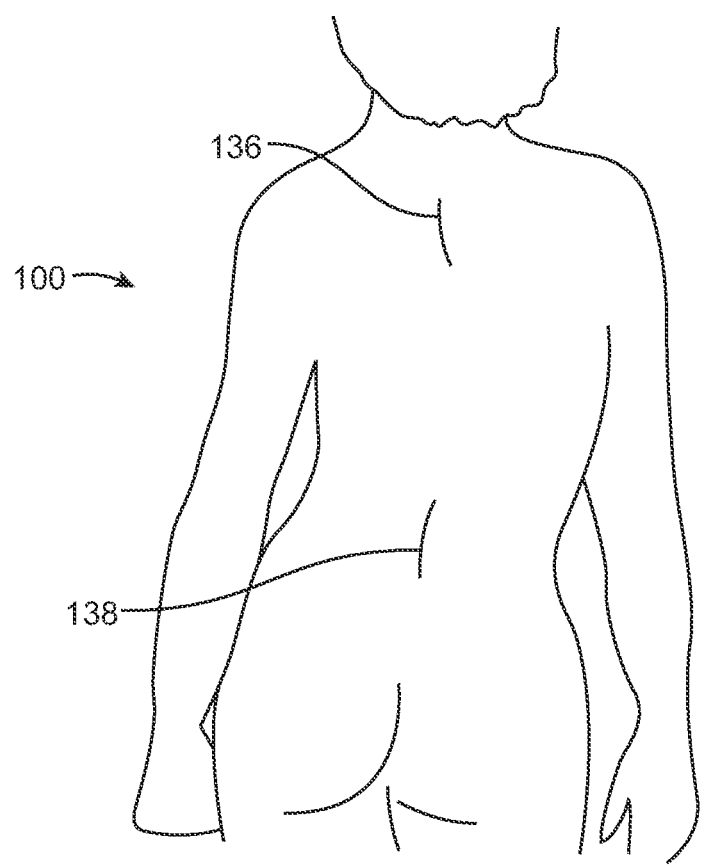
FIG. 3 illustrates the small incisions made during scoliosis non-fusion surgery of the inventive embodiments.

In many Adolescent Idiopathic Scoliosis (AIS) patients with a Cobb angle of 40° or greater, spinal fusion surgery is typically the first option. Alternatively, non-fusion surgery may be performed, for example with the distraction device 200 of FIG. 4. FIG. 3 illustrates an upper incision 136 and a lower incision 138 formed in the patient 100 which is typically made during non-fusion scoliosis surgery.

Figure 4:
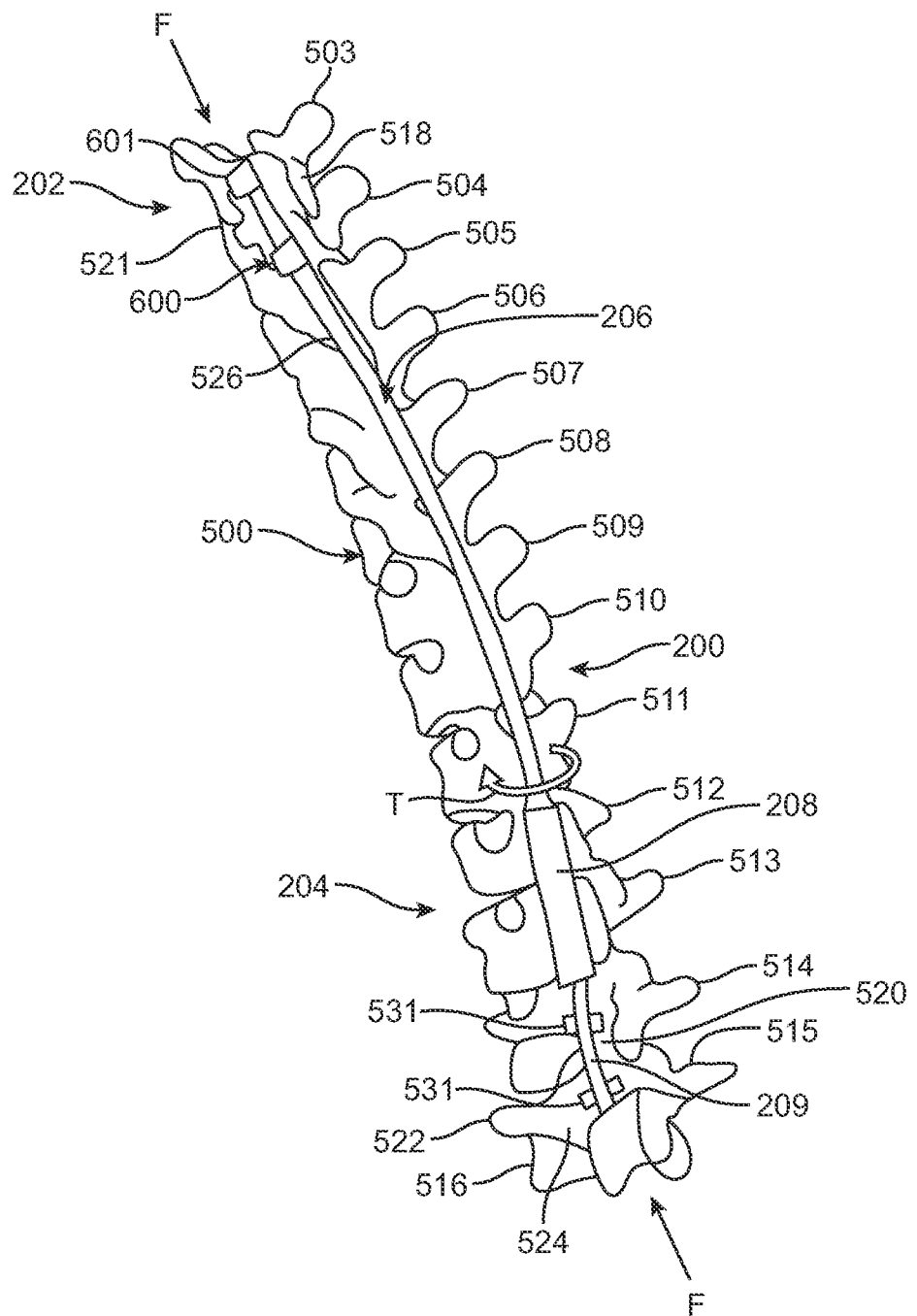
FIG. 4 illustrates an exemplary distraction device mounted on the spine of a subject.

FIG. 4 illustrates a distraction device 200 for treating scoliosis according to one embodiment of the invention. The distraction device 200, which is an implantable device, is fixated at its upper end 202 and lower end 204 to the patient's spine 500. The illustrated example of the spine 500 includes the particular thoracic and lumbar vertebrae that typically encompass a scoliotic curve, for example the curve of a patient with adolescent idiopathic scoliosis. The T3 through T12 thoracic vertebrae, 503, 504, 505, 506, 507, 508, 509, 510, 511, 512, respectively and the L1 through L3 vertebrae, 513, 514, 515 are depicted in FIG. 4, not in a severe scoliotic condition, but in a very slight residual curve that represents a modest curve that has been partially or completely straightened during the implantation procedure.

Each vertebra is different from the other vertebra by its size and shape, with the upper vertebra generally being smaller than the lower vertebra. However, generally, the vertebrae have a similar structure and include a vertebral body 516, a spinous process 518, 520, laminae 526, transverse processes 521, 522 and pedicles 524. In this embodiment, the distraction device 200 includes a distraction rod 206 which is adjustable (lengthwise) via a coupled adjustable portion 208. The distraction device 200 also includes a lower short rod 209. The distraction device 200 is fixated to the spine 500 via hooks 600, 601 at the upper end 202 of the distraction rod 206. Alternatively, a clamp may be secured around an adjacent rib (not shown) or rib facet. In sill another alternative, a pedicle screw system may be used.

Referring back to FIG. 4, the distraction device 200 is illustrated as being fixated to the spine 500 with a pedicle screw system 531, which attaches directly to the lower short rod 200. The distraction rod 206 is shown after it has been bent into a kyphotic curve, and the lower short rod is shown after it has been bent into a lordotic curve. As explained in more detail below. The adjustable portion 208 preferably contains a magnetic assembly having a permanent magnet configured to drive a lead screw that, depending on the direction of rotation of the internal magnet, will extend or retract the distraction rod 206 using the adjustable portion 208. Lengthening of the distraction rod 206, for example, will impart a distraction force to the spine 500. Retracting the distraction rod 206 will lower or remove the distraction force on the spine 500, for example if too high a distraction force causes pain or complications.

Because a scoliotic spine is also rotated (usually the center section is rotated to the right in AIS patients), the non-fusion embodiment presented here allows de-rotation of the spine 500 to happen naturally, because there is no fixation at the middle portion of the distraction device 209.

In order to further facilitate this de-rotation, the distraction device 200 may allow for free rotation at its ends. For example, the adjustable portion 208 may be coupled to the spine via an articulating joint. U.S. Patent Application Publication Nos. 20090112207 and 20100094302, both of which are incorporated by reference, describe various articulating interfaces and joints that may be utilized to couple the adjustable portion 208 to the connecting rods or the like. These Publications further describe various distraction rod embodiments and methods of use that may be used with inventions described herein.

As noted, the distraction rod 206 and the lower short rod 209 may be bent by the user (or supplied pre-curved) with the typical shape of a normal saggital spine, but it should also be noted that the curve may be slightly different than standard scoliosis fusion instrumentation, because in the non-fusion embodiment described herein, the distraction device 200 is not usually flush with the spine but rather is placed either subcutaneous or sub-fascial, and thus is not completely below the back muscles, in these less invasive methods, the only portions of the distraction device 200 that are designed to be placed below the muscles are the hooks 600, 601 and the portion of the distraction rod 206 immediately adjacent the hooks 600, 601, the pedicle screw system 531 and the lower short rod 209. Thus, FIG. 4 illustrates an embodiment in which the bulk of the hardware associated with the distraction device 200 is placed over the muscle. It should be understood, however, that in alternative configurations, any other part of the entire implantable embodiment may be placed under the muscle (i.e., sub-muscular). It should be appreciated that a much smaller amount of muscle needs to be dissected during the procedure in comparison with current fusion procedures. This will allow for a much shorter procedure, much less blood loss, much quicker recovery, and less time in the hospital/less risk of infection.

FIGS. 5A-5C illustrate cross-sectional views of the interface of the distraction rod 206 with the adjustable portion 208. FIG. 5A is a cross-sectional view of the distraction rod 206 and adjustable portion 208 taken along a perpendicular axis to the longitudinal axis of the distraction rod 206. FIG. 5B illustrates a cross-sectional view of the distraction rod 206 and the adjustable portion 208 taken along the line B'-B of FIG. 5A. FIG. 5C illustrates an enlarged cross-sectional view of detail C of FIG. 5B. As best seen in FIG. 5C, an end 210 of the distraction rod 206 includes an elongate recess 212. The elongate recess 212 may have a length of around 60 mm. The recess 212 is dimensioned to receive a lead screw 260. The lead screw 260 may be made from a high strength material such as, for example, titanium. At least a portion of the lead screw 260 includes external threads 262 that are configured to engage with a nut 214 integrated into the recess 212. The nut 214 provides a threaded portion on the recess 212 of the distraction rod 206. The lead screw 260 may have, for example, 80 threads per inch although more or less could be used. The nut 214 may includes threads or a chamfered surface 216 on the outer diameter in order to better ensure a secure attachment to the inner diameter of the recess 212 of the distraction rod 206. For example, the nut 214 may be bonded to the distraction rod 206 using an adhesive such as EPOTEK 353ND, available from EPOXY TECHNOLOGY, INC., 14 Fortune Drive, Billerica, Mass. This allows the distraction rod 206 to be fabricated from a single piece of stronger material. It also provides for clearance between the lead screw 260 and internal diameter of the distraction rod 206. Alternatively, a threaded portion may be directly formed in the recess 212 without the aid of a separate nut 214. A radially-poled cylindrical magnet 254 is part of a magnetic assembly 236 comprising a first cup 240 and a second cup 242. The first and second cups 240, 242 are made from titanium. This entire magnetic assembly 236 is attached to the lead screw 260, for example by a high strength pin 238 which is placed through a hole in the lead screw 260 and a receptacle 244 in the first cup 240. This couples the cylindrical magnet 254 to the lead screw 260. The cylindrical magnet 254 typically has two poles, a North and a South that are radially arrayed, as depicted in FIG. 5D. The cylindrical magnet may comprise a rare earth material, such as Neodymium-Iron-Boron. The cylindrical magnet 254 is attached to a thrust bearing 250 and a radial bearing 246, which allow the low friction rotation of the cylindrical magnet 254, and this aids the low friction rotation of the lead screw 260 within the nut 214. This allows for the non-invasive coupling of an external moving magnetic field, in order to non-invasively distract the distraction device 200, allowing the distraction rod 206 to telescopically extend from the adjustable portion 208, and impart an increased distraction force on the spine 500. The moving magnetic field may be supplied by one or more rotating magnets, for example as part of a motor-driven external device. Alternatively, the moving magnetic field may be produced by an electromagnetic coil. The lead screw 260 and nut 214 combination allows for a device that can be distracted or retracted. The device is retracted by making the external moving magnetic field move in the opposite rotational direction. This is an advantage, for example in the case of a patient that has accidentally been over distracted. The distraction device 200 may then be retracted somewhat, until the patient is at the preferred distraction amount. An elastomeric o-ring 234 creates a dynamic seal between the timer surface of the adjustable portion 208 and the distraction rod 206. This o-ring resides inside a recess 232 of an o-ring gland 230 within the interior of the adjustable portion 208.

The low friction lead screw 260 and nut 214 combination combined with the low friction hearings 250, 246 minimize the torque that needs to be applied on the cylindrical magnet 254. Thus, they also minimize the required size of the cylindrical magnet 254, because they minimize the magnetic force required to make the cylindrical magnet 254 turn. However, these same advantages also may make the assembly prone to lose some of the distraction length as the patient moves through daily activity. For example (returning to FIG. 4), it may be possible for a pattern's movement to create a "screw-like" motion which is capable of slowly retracting the distraction rod 206 in relation to the adjustable portion 208, and thus shortening the distraction device 200 by multiples of very small movements. For example, in the process of walking, running, bending or other movements, a patient may place a compressive bending force (F) on the distraction device 200, In these movements, the patient may also place a torque (T) between the two ends of the distraction device 200, for example, the two ends at the portions that are secured to the spine 500. In FIG. 4, a positive value of torque (T) denotes a right-hand mode, in which the distraction rod 206 is given energy to move in the direction of the arrow at torque (T) while the adjustable portion is given energy to move in the opposite circumferential direction. A negative value of torque (T) would represent the opposite, left hand motion. If there are no internal features in the distraction device 200 to limit the circumferential motion of the distraction rod 206 in relation to the adjustable portion 208, the a positive value of torque (T) will cause the distraction rod 206 and adjustable portion 208 to circumferentially displace until, for example, the torsional movement in the patient stops, either willingly, or by the physical limitations in the spine or the rest of body. If the patient's movements cycle between bending and twisting, and therefore, between the Force (F) and torque (T) depicted, they may do so in such a way as to cause a multiplicity of slight angular turns of the lead screw 260 in one direction in relation to the nut 214, without compensatory turns in the opposite direction. For example, referring to FIG. 6, in laboratory testing, a distraction device 200 was secured with set screws 217, 219 in a distraction loss tester 211 having simulated vertebrae 213, 215 in order to place controlled axial compressive force (F) and a controlled twisting torque (T) on the distraction device 200. One cycle of the program consisted of a 100 Newton compressive force (F), followed by a 0.81 Newton-meter torque (T), after which the compressive force (F) was completely released (0 Newton) and then an opposite torque (−0.81 Newton-meter) (−T) was placed. These parameters are considered extreme in relation to a typical patient's movements, but are effective in estimating "worst-case" operation, for example, if the distraction device 200 were being used as a single device within a very active patient. A distracted distraction device 200 tested under these parameters was able to lose several mm of distraction length after about 10,000 cycles, which is estimated be the equivalent of about one week in a patient (though actual patient movements are usually much more variable).

Figure 7A:
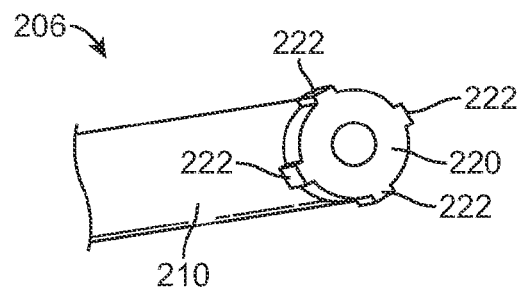
FIG. 7A illustrates a perspective view of one end of a distraction rod illustrating the splined tip.

In reality, the preferred design for a distraction device 200, does not allow significant circumferential motion between the distraction rod 206 and the adjustable portion 208. FIG. 7A illustrates a perspective view of the splined tip 220 of the distraction rod 206. The splined tip 220 is illustrated with four (4) protrusions 222 that interface with four (4) corresponding longitudinal grooves 224 (two pairs in symmetric opposition) formed inside a tubular housing 226 (illustrated in FIGS. 7B-D) of adjustable portion 208. The longitudinal grooves 224 may be formed by wire EDM machining or by broaching. While FIGS. 7A-7D illustrate an embodiment that uses four (4) protrusions 222 along with four (4) longitudinal grooves 224 there may be more or fewer. The tight tolerance of the splined tip 220 with the longitudinal grooves 224 keeps the distraction rod 206 centered within the tubular housing 226. In addition, the combination of the splined tip 220 and corresponding grooves 224 act as an anti-rotation feature that prevents the distraction rod 206 from rotating relative to the tubular housing 226. This may be necessary to allow the distraction device 200 to be "rigidized" in the event the device is used in fusion applications, instead of the non-fusion applications described. For example, in a fusion application, it is desired that the spine 500 not be able to flex or rotate much during the months that the fusion is taking place. In either the fusion applications or the non-fusion applications, the anti-rotation features are intended to limit inadvertent extension and/or retraction of the distraction rod 206 resulting from, for instance, patient movements.

Figure 7B:
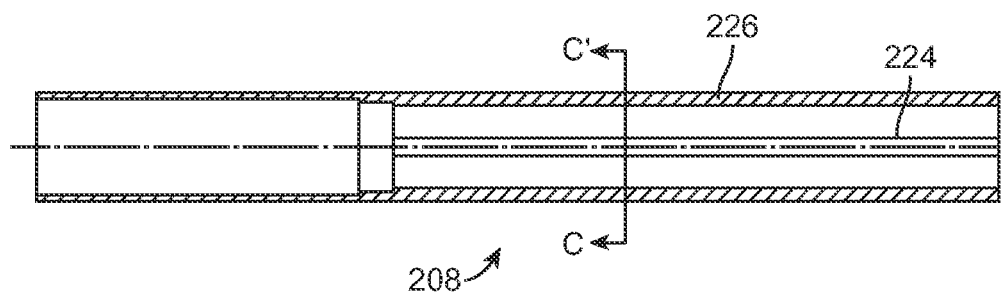
FIG. 7B is a side cross-sectional view of the tubular housing with the lead screw and magnetic assembly removed for clarity.
Figure 7C:
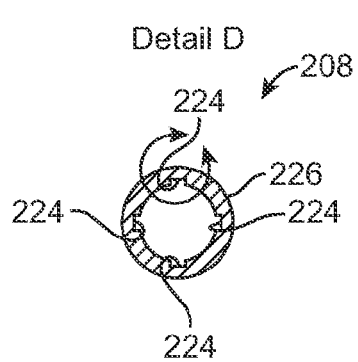
FIG. 7C is a cross-sectional view of the tubular housing taken along the line C'-C in FIG. 7B.
Figure 7D:
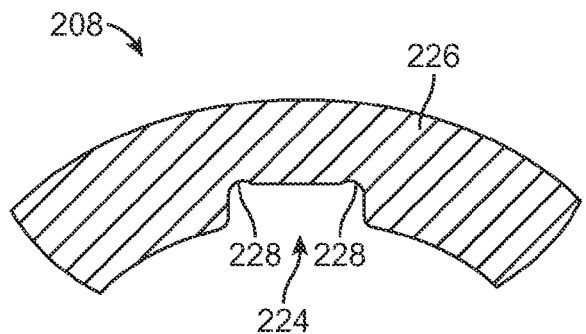
FIG. 7D illustrates a magnified view of detail D of FIG. 7C.

FIG. 7C is a cross-sectional, view of the tubular housing 226 taken along the line C'-C in FIG. 7B. FIG. 7D illustrates a magnified view of detail D of FIG. 7C. In this illustrated embodiment, as best seen in the detailed view of FIG. 7D, small reliefs 228 are incorporated into the sides or corners of the longitudinal grooves 224. These reliefs 228 may be slight over cut wire EDM notches that prevent the corners of the protrusions 222 from contacting the inner wall of the tubular housing 226. Less contact between the protrusions 222 and the longitudinal grooves 224 results in less frictional forces and reduces the likelihood of binding. Optionally, the tops of the protrusions 222 could be curved, for example, cut from a diameter instead of a square. This rounding of the protrusions 222 would keep the protrusions 222 from binding with the longitudinal grooves 224 when torsional stresses are imparted between the distraction rod 206 and the adjustable portion 208. This optional modification makes the distraction rod 206 easier to manufacture and eliminates the need for the relief 228 overcuts. At the maximum amount of axial distraction length, the protrusions 222 butt up against a stop 231 (as seen in FIG. 5C), so that the distraction rod 206 terminates its axial movement in relation to the adjustable portion 208.

Figure 6:
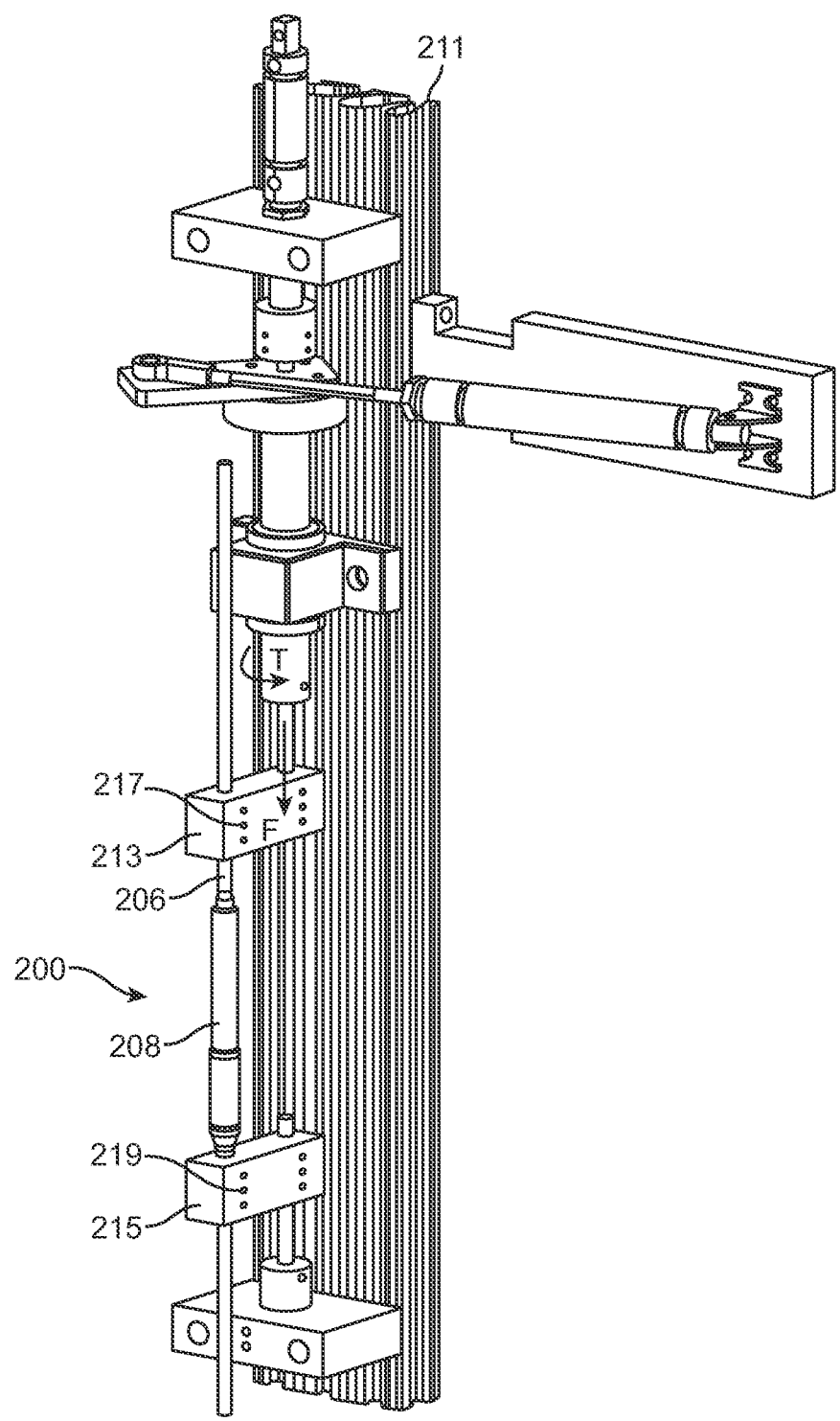
FIG. 6 illustrates a distraction device being tested within a distraction loss tester.

The anti-rotation features of FIGS. 7A-7D are effective in severely minimizing distraction loss in a large variety of patient applications, however, under severe conditions, such as those described in FIG. 6, a distraction device 200 with these features may still lose as much as 1 mm over 10,000 cycles. An additional design improvement which takes advantage of the magnetic poles (FIG. 5D) of cylindrical magnet 254 will now be described, as a way to severely limit distraction loss, even in the most severe performance conditions.

Figure 8:
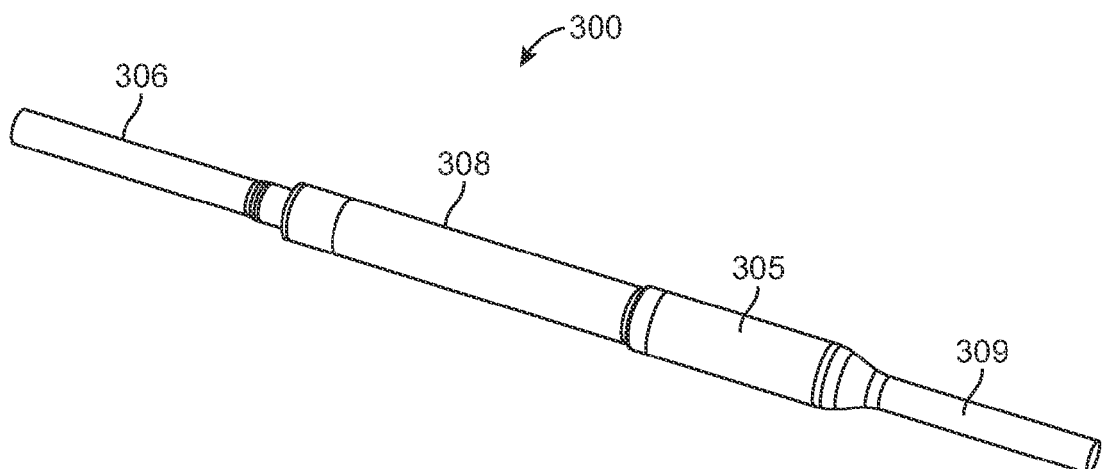
FIG. 8 illustrates an embodiment of a distraction device having a maintenance member.
Figure 9:
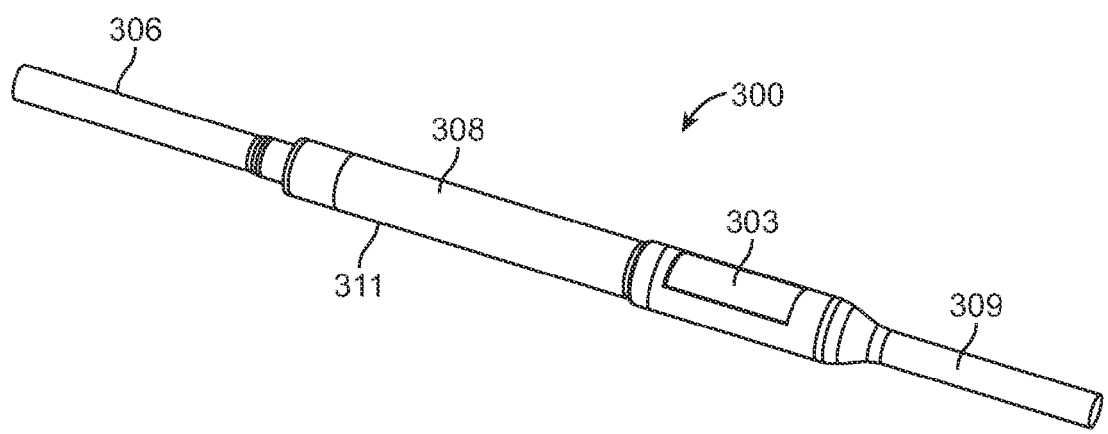
FIG. 9 illustrates an embodiment of the distraction device of FIG. 8 with a cover sleeve removed and showing the maintenance member.
Figure 10A:
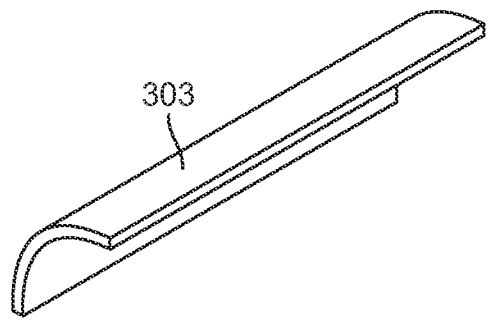
FIG. 10A illustrates the maintenance member of FIGS. 8 and 9.
Figure 10B:
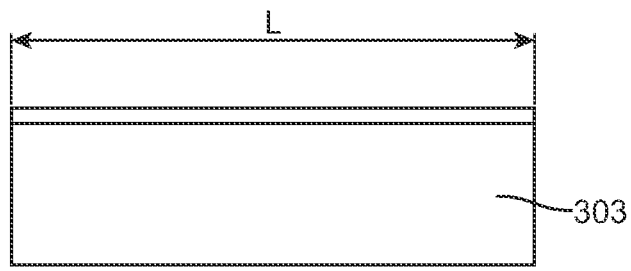
FIG. 10B illustrates a side view of the maintenance member of FIG. 10A.
Figure 10C:
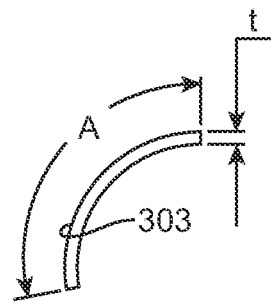
FIG. 10C illustrates an end view of the maintenance member of FIG. 10A.

FIG. 8 is a view of a distraction device 300 which does not allow distraction loss when subjected to the severe testing parameters described above. Distraction device 300 has distraction rod 306 and adjustable portion 308, and the device is identical to the distraction device 200 described in the prior figures, except that it also comprises a maintenance member 303 as seen in FIG. 9. A lower short rod 309 extends from the adjustable portion 308 in a direction opposite the distraction rod 306. FIG. 9 shows the maintenance member 303 with external cover 305 removed. FIG. 8 shows the completed device with the maintenance member 303 completely covered by external cover 305. The external cover 305 is made of Titanium or Titanium alloy, for example, and is welded to the exterior of the adjustable portion 308 (also Titanium or titanium alloy) to completely isolate maintenance member 303 from the patient. The maintenance member 303 is made from a magnetically permeable material such as iron or mu-metal (75% nickel, 15% iron, plus copper and molybdenum). The maintenance member may also be made from a biocompatible and typical implant material such as 400 series stainless steel, for example 420 stainless steel. Alternatively to being isolated within the double wall of the adjustable portion 308 of the distraction device 300 as depicted, a portion of the outer wall of the adjustable portion 308 may be made from a magnetically permeable material, such as 400 series stainless steel and the remainder of the outer wall may be made of a material like Titanium or Titanium alloy, without significant magnetic properties. The maintenance member 303 may also be coated with a biocompatible material. As illustrated in FIGS. 10A, 10B and 10C, the maintenance member 303 has an arcuate shape with an arc of less than 360°. In some embodiments, the arc may be less than 180° or 120°. In the embodiment of FIGS. 10A, 10B and 10C, the arc (A) is approximately 99° although a smaller arc may be used. The length (L) of the maintenance member 303 is 19 mm in the embodiment depicted. In the adjustable portion 308 of the distraction device 300, the maintenance member 303 is located axially in the same portion as the cylindrical magnet 254. Because of its magnetically permeable characteristics, the maintenance member 303 will most strongly attract the north pole or the south pole of the cylindrical magnet 254, but will not attract the portion which is halfway between the north pole and south pole. Referring to FIG. 10C, the maintenance member 303 preferably has a thickness (t) of at least 0.2 mm, and more preferably at least 0.3 mm. A typical thickness of the maintenance member 303 is 0.48 mm (0.019 inches) or less. In the configuration depicted, the radius of curvature of the concave surface of the maintenance member 303 is 4.5 mm but this radius of curvature could be less. The diameter of the adjustable portion 308 is 10.5 mm over the external cover 305, and is 9.0 mm over the non-magnetic portion 311.

Figure 11A:
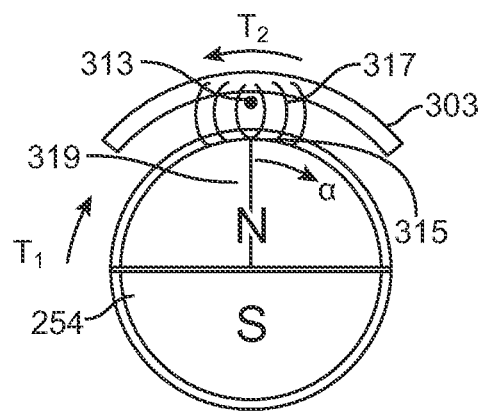
FIG. 11A illustrates the magnetic and mechanical forces acting on a cylindrical magnet.
Figure 11B:
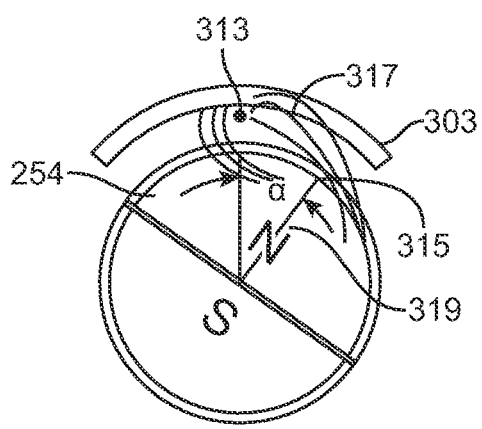
FIG. 11B illustrates the cylindrical magnet being torqued to a finite amount away from its magnetic orientation with a maintenance member.
Figure 11C:
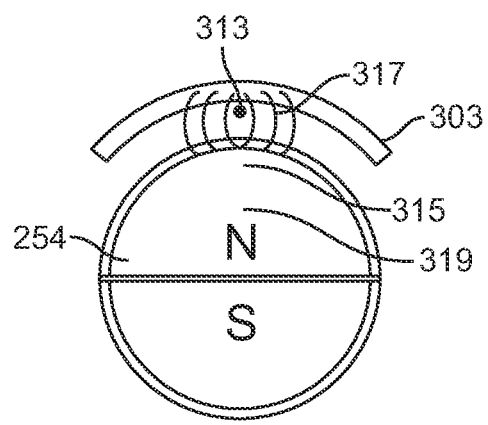
FIG. 11C illustrates the cylindrical magnet after being aligned from a torque applied on its north pole by a maintenance member.

FIGS. 11A, 11B and 11C demonstrate the effect of the maintenance member 303 in maintaining the circumferential orientation of the cylindrical magnet 254, and thus the circumferential orientation of the lead screw 260 (FIG. 5C), and thus the amount of axial distraction in the distraction device 300. In FIG. 11A, the centerpoint 315 of the north pole 319 of the cylindrical magnet 254 aligns with the center of mass 313 of the maintenance member 303. When patient movement causes a first torque T1 to be applied to the cylindrical magnet 254, a magnetic corrective torque T2 based on the magnetic field 317 between the maintenance member 303 and the cylindrical magnet 254 acts upon the cylindrical magnet 254. If the first torque T1 is less than the corrective torque T2, then the magnet will not be displaced. It should be noted however that the corrective torque T2 increases as the displacement angle α increases. When a significantly large torque is placed on the cylindrical magnet 254 (FIG. 11B), for example in combination with a significant compressive force on the distraction device 300, the lead screw will slightly turn, and thus the magnet will slightly turn. Because the maintenance member 303 is present, the magnetic field 317 will return the cylindrical magnet 254 to its original circumferential orientation (FIG. 11C), for example when the compressive force on the distraction device 300 is released.

Figure 12:
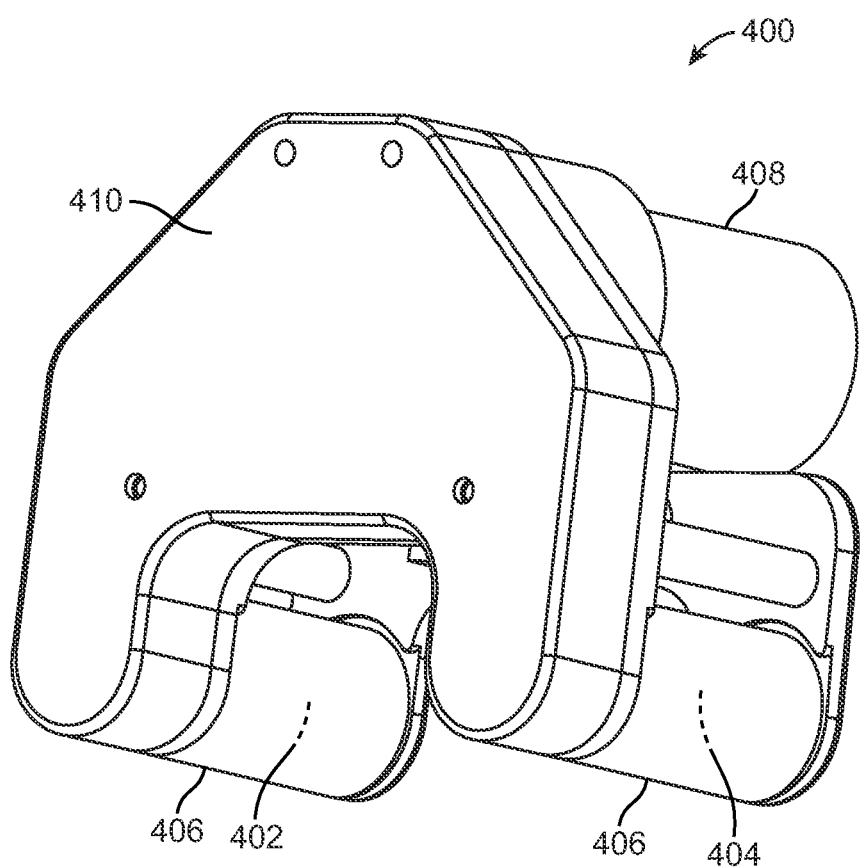
FIG. 12 illustrates and external adjustment device that is used with the distraction devices described herein.

It should be noted that the distraction force which can be achieved in the distraction device 300 will be somewhat less with the maintenance member 303 in place than without it. For example, a distraction device 300 that achieves a distraction force of 220 Newtons without the maintenance member 303 will achieve a distraction force of about 195 Newtons (12% reduction) with the maintenance member 303 in place. The circumferential orientation of the distraction device 300, and thus the circumferential orientation of the maintenance member 303 within the body, does not cause a large difference in the ability to distract the distraction device 300, because typically very large, overpowering magnets are used externally to distract the implanted distraction device 300. Typically, two such magnets are located in an external adjustment device and are rotated to impart rotational motion to the cylindrical magnet 254. Particular details on the nature of the external adjustment devices that can be used in connection with the distraction devices described herein are disclosed, for example, in. U.S. Patent Application Publication Nos. 2009/0112207, 2010/0094302, 2010/0121323, and U.S. patent application Ser. No. 13/172,598, all of which are incorporated by reference herein. FIG. 12 illustrates an external adjustment device 400 according to one embodiment that includes two permanent magnets 402, 404 contained within respective covers 406. Each permanent magnet 402, 404 is rotatable within its respective cover 406 and provides a moving magnetic field. A motor 408 is mechanically engaged to the permanent magnets 402, 404 via a transmission (not shown) contained within a housing 410 of the external adjustment device 400

Distraction devices constructed with the maintenance member 303 as described, having a cylindrical magnet 254 diameter of less than 9 mm, have been tested in the severe 100

Newton compressive force/0.81 Newton-meter torque cyclic regime as described, and have maintained their distraction amount over hundreds of thousands of cycles. These devices have also been implanted in patients who are physically active, and the implanted devices have maintained their distraction amount over several months of patient activity.

Another advantage of the maintenance member 303 is that, when distracting the distraction device, the device is adjusted to very specific gradations. For example two per rotation of the magnet, when either the south pole or the north pole aligns with the center of mass 313 of the maintenance member 303. For example, these gradations may be equal to approximately 0.16 mm in the present case, or even more preferably 0.10 mm or 0.20 mm.

In one alternative embodiment, there are two or more magnetic members 303, for example, one magnetic member matched with each of the poles of the cylindrical magnet. In another alternative embodiment, the cylindrical magnet may be replaced by two or more magnetically permeable components, each spanning less than 180° of an arc, and the maintenance member may be replaced with a magnet. The maintenance member may include a number of configurations including a plate, a wire, a series of balls, or any other configuration of magnetically permeable material.

Figure 14:
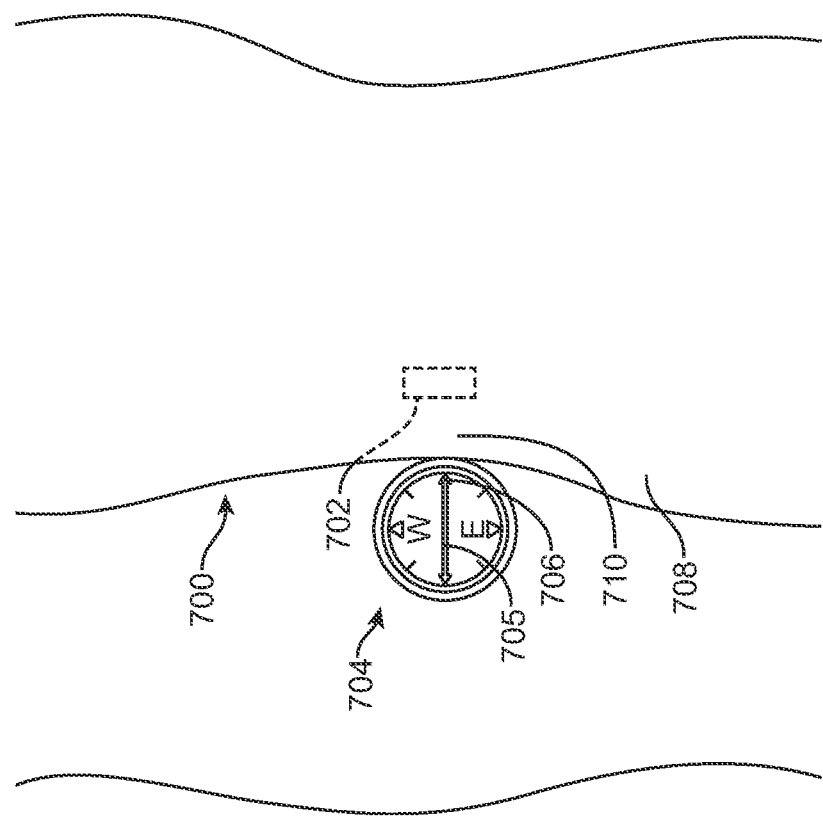
FIG. 14 illustrates a method of using a magnetic compass to locate an implanted magnet with the magnetic compass in a final location.
Figure 13:
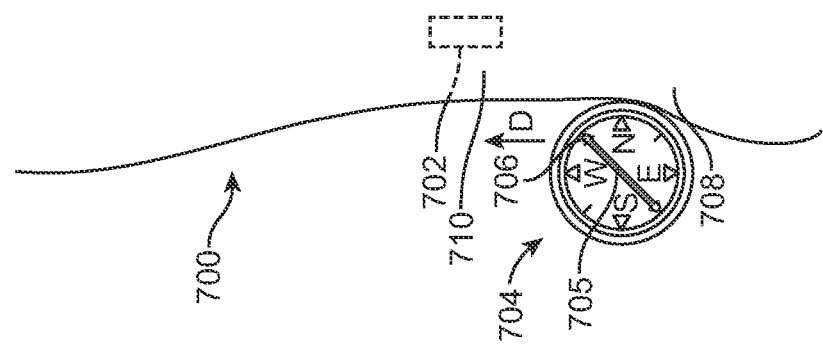
FIG. 13 illustrates a method of using a magnetic compass to locate an implanted magnet with the magnetic compass in an initial location.

FIGS. 13 and 14 describe a method for locating an implanted magnet 702 within a patient 700. This can be used for any magnetic medical device, but will be described specifically for a distraction system containing a magnet. The method utilizes standard magnetic compasses, which can be obtained very easily all over the world. The method consists of providing a magnetic compass 704, providing instructions for a user for using the magnetic compass 704 to locate an implanted magnet 702 within the distraction system, wherein the instructions instruct the user to place the magnetic compass 704 in proximity to a general area 708 of the patient's skin near the expected location of the implanted magnet 702 of the distraction system, and for the user to view the direction that a magnetized pointer 706 of a needle 705 of the magnetic compass 704 points, and for the user to determine that the magnetized pointer 706 is pointing towards the implanted magnet 702, wherein the instructions further instruct the user to move the magnetic compass 704 along the skin of the patient until the magnetized pointer 706 is perpendicular to the skin (FIG. 14), and for the user to determine that the location 710 to which the magnetic compass 704 is moved is the correct location for placing an external adjustment device 400 which is enabled to cause the distraction system to magnetically distract.

As illustrated in FIGS. 13, and 14, the patient 700 has an implanted magnet 702 which is implanted near the lower back area, and the patient lies prone while the magnetic compass 704 is held to the side of the patient, with the needle 705 able to spin on the horizontal plane, and with the magnetic compass 704 held at approximately the same horizontal plane as the depth of implantation of the implanted magnet 702. In FIG. 13, the magnetic compass 704 is initially held further distal (towards the feet) than the implanted magnet 702, with, the magnetized pointer 706 of the needle 705 pointing at an angle towards the implanted magnet 702. The magnetic compass 704 is moved in direction (D) until it is located as in FIG. 14, with the magnetized pointer 706 of the needle 705 perpendicular to the skin. Using the method described, small implanted magnets may be successfully located. For example, the location of a magnet having a mass of 5.4 grams can be correctly identified with a standard low-cost magnetic compass at an implant depth of as much as 10 cm.

While embodiments have been shown and described, various modifications may be made without departing from the scope of the inventive concepts disclosed herein. The invention(s), therefore, should not be limited, except to the following claims, and their equivalents.

What is claimed is:

1. A distraction system comprising:
   a distraction rod having a first end configured for placement within a patient at a first location and a second end having a threaded portion;
   an adjustable portion configured for placement within the patient at a second location, the adjustable portion comprising a driving element configured to be non-invasively rotated, the driving element rotationally coupled to a lead screw, the lead screw threadingly engageable with the threaded portion of the distraction rod; and
   a maintenance member in proximity to but physically isolated from the driving element, wherein the maintenance member is configured to substantially maintain circumferential orientation of the driving element when a torque of 0.81 Newton-meter is placed between the distraction rod and the adjustable portion.

2. The distraction system of claim 1, wherein the driving element comprises a magnet having at least one pole and wherein the maintenance member comprises a magnetically permeable member configured to attract the at least one pole of the magnet when the at least one pole of the magnet is in proximity to the magnetically permeable member.

3. The distraction system of claim 2, wherein the magnetically permeable member covers an arc of less than 360° of the adjustable portion.

4. The distraction system of claim 3, wherein the magnetically permeable member covers an arc of less than 180° of the adjustable portion.

5. The distraction system of claim 1, wherein the maintenance member comprises a ferrous material.

6. A distraction system comprising:
   a distraction rod having a first end configured for placement within a patient at a first location and a second end having a threaded portion;
   an adjustable portion configured for placement within the patient at a second location, the adjustable portion comprising a driving element configured to be non-invasively rotated, the driving element rotationally coupled to a lead screw, the lead screw threadingly engageable with the threaded portion of the distraction rod; and
   a maintenance member which does not contact the driving element throughout a full rotation of the driving element, wherein the maintenance member is configured to substantially inhibit rotation of the driving element when a torque of 0.81 Newton-meter is placed between the distraction rod and the adjustable portion.

7. The distraction system of claim 6, wherein the driving element comprises a magnet having at least one pole and wherein the maintenance member comprises a magnetically permeable member configured to attract the at least one pole of the magnet when the at least one pole of the magnet is in proximity to the magnetically permeable member.

8. The distraction system of claim 7, wherein the magnetically permeable member covers an arc of less than 360° of the adjustable portion.

9. The distraction system of claim 8, wherein the magnetically permeable member covers an arc of less than 180° of the adjustable portion.

10. The distraction system of claim 6, wherein the maintenance member comprises a ferrous material.

11. A distraction system comprising:

a distraction rod having a first end configured for placement within a patient at a first location and a second end having a threaded portion;

an adjustable portion configured for placement within the patient at a second location, the adjustable portion comprising a driving element configured to be non-invasively rotated, the driving element rotationally coupled to a lead screw, the lead screw threadingly engageable with the threaded portion of the distraction rod; and a maintenance member physically isolated from the driving element, wherein the maintenance member is configured to substantially maintain circumferential orientation of the driving element when a torque of 0.81 Newton-meter is placed between the distraction rod and the adjustable portion.

12. The distraction system of claim 11, wherein the driving element comprises a magnet having at least one pole and wherein the maintenance member comprises a magnetically permeable member configured to attract the at least one pole of the magnet when the at least one pole of the magnet is in proximity to the magnetically permeable member.

13. The distraction system of claim 12, wherein the magnetically permeable member covers an arc of less than 360° of the adjustable portion.

14. The distraction system of claim 11, wherein the maintenance member comprises a ferrous material.

15. A distraction system comprising:

a distraction rod having a first end configured for placement within a patient at a first location and a second end having a threaded portion;

an adjustable portion configured for placement within the patient at a second location, the adjustable comprising a driving element configured to be non-invasively rotated, the driving element rotationally coupled to a lead screw, the lead screw threadingly engageable with the threaded portion of the distraction rod; and a maintenance member which does not contact the driving element throughout a full rotation of the driving element, wherein the maintenance member is configured to substantially inhibit rotation of the driving element when a torque of 0.81 Newton-meter is placed between the distraction rod and the adjustable portion, wherein the maintenance member is in proximity to the driving element.

* * * * *